United States Patent [19]

Suggitt et al.

[11] 4,127,471
[45] Nov. 28, 1978

[54] HYDROCRACKING ALKYLAROMATIC-CONTAINING HYDROCARBONS AT MILD CRACKING CONDITIONS AND THEN SUBJECTING THE ALKYLAROMATIC HYDROCARBON TO ALKYL TRANSFER

[75] Inventors: Robert M. Suggitt, Wappingers Falls; Sheldon Herbstman, Spring Valley, both of N.Y.

[73] Assignee: Texaco Inc., New York, N.Y.

[21] Appl. No.: 819,901

[22] Filed: Jul. 28, 1977

[51] Int. Cl.$^2$ .................. C10G 13/06; C07C 15/02
[52] U.S. Cl. .................. 208/60; 208/58; 208/62; 208/135; 260/672 T
[58] Field of Search .................. 208/58, 60, 59, 62; 260/672 R, 672 T

[56] References Cited

U.S. PATENT DOCUMENTS

| | | | |
|---|---|---|---|
| 3,215,617 | 11/1965 | Burch et al. | 208/59 |
| 3,254,017 | 5/1966 | Arey et al. | 208/59 |
| 3,317,622 | 5/1967 | Hoertz et al. | 260/672 R |
| 3,476,821 | 11/1969 | Brandenburg et al. | 260/672 T |
| 3,505,208 | 4/1970 | Vaell | 208/111 |
| 3,554,898 | 1/1971 | Wood et al. | 208/59 |
| 3,565,788 | 2/1971 | Foucher et al. | 208/111 |
| 3,780,121 | 12/1973 | Suggitt et al. | 260/672 T |
| 3,780,122 | 12/1973 | Pollitzer | 260/672 T |
| 3,780,123 | 12/1973 | Suggitt et al. | 260/672 T |

*Primary Examiner*—Delbert E. Gantz
*Assistant Examiner*—G. E. Schmitkons
*Attorney, Agent, or Firm*—Thomas H. Whaley; Carl G. Ries; Carl G. Seutter

[57] ABSTRACT

Hydrocarbon conversion is effected by hydrocracking a charge stock at mild cracking conditions followed by alkyl transfer typically transalkylation or disproportionation or isomerization under conditions conducive to extended catalyst life.

17 Claims, No Drawings

HYDROCRACKING ALKYLAROMATIC-CONTAINING HYDROCARBONS AT MILD CRACKING CONDITIONS AND THEN SUBJECTING THE ALKYLAROMATIC HYDROCARBON TO ALKYL TRANSFER

FIELD OF THE INVENTION

This invention relates to the preparation of hydrocarbons. More specifically, it relates to hydrocarbon conversion processes typified by transalkylation or disproportionation particularly characterized by extended catalyst life.

BACKGROUND OF THE INVENTION

As is well known to those skilled in the art, various aromatic fractions containing light alkylaromatics (benzene, toluene, xylene, etc.) commonly in the $C_6$ to $C_{12}$ range may be converted into other desired fractions. Such charge materials may be derived from various sources including petroleum refinery sources, coking of coal, etc. More specifically, such streams may be recovered from the so-called coal-tar by-products, from tar sands, from petroleum refinery processes, etc. Such streams are preferably treated to lower the content of nitrogen (including organic nitrogen) to less than 10 ppm, more preferably to below 1 ppm, prior to further treating.

During petroleum processing, for example, $C_6$ to $C_{12}$ fractions containing alkylaromatic hydrocarbons may be recovered as components of various streams. In the case of catalytic reforming, the reformate (after extraction of undesired fractions including aliphatics) may contain a $C_6$ to $C_{12}$ alkylaromatic hydrocarbon fraction. A typical alkylaromatic fraction which may be obtained contains predominantly $C_6$ to $C_9$ hydrocarbons. Still another aromatic fraction which may be obtained, referred to as crude xylenes, actually contains hydrocarbons having 7-9 carbon atoms.

Refinery operations in which high grade gasolines are to be produced may recover an aromatic fraction containing predominantly 6-8 carbon atoms — referred to as a BTX fraction — containing substantial quantities of benzene, toluene, xylenes and ethylbenzene.

In processing each of these fractions, it is commonly desired to recover each of the components to permit most efficient utilization of the separated components. In the case of the crude xylenes, it may be desirable to recover substantially pure xylenes free of $C_7$ and $C_9$ cuts.

In the case of the $C_6$–$C_9$ charge, it may be desirable to recover the toluene to permit, e.g. its use in gasolines and to thereby upgrade the latter — in particular, to increase the back-end volatility which improves the drivability of new cars during engine warmup. More particularly, the possibility of more severe restrictions on lead anti-knock content and on the end point of motor naphtha raises a problem which may be solved by the presence of increasing proportions of toluene and $C_8$ aromatics (xylenes and ethylbenzene) in motor fuels with decreased proportion of benzene and $C_9$ aromatics.

Treatment of these typical streams to upgrade them may commonly include transalkylation wherein typically benzene and $C_9$ and $C_{10}$ aromatics may react to produce increased yield of desired toluene and $C_8$ aromatics. Similarly $C_8$ and $C_9$ stocks can be prepared by transalkylating toluene with $C_{10}$ and $C_{11}$ aromatics.

Transalkylation for example may be carried out in the presence of a catalyst which may include a Group VIII metal on a solid acidic support. Typical of such solid acid catalysts may be that including:

15% — alumina matrix
85% — 0%–12% cobalt sulfide on 40:1 $SiO_2:Al_2O_3$ acid-leached mordenite As alkyl transfer is carried out under predetermined conditions of temperature, pressure, flow rate, etc., it is found that the yield of desired product decreases with time. Typically, for example, when using the above-mentioned acid mordenite catalyst in transalkylation at 650° F., 800 psig and total LHSV (equimolor amounts of benzene and xylene) of 6, the initial toluene yield may be 40%. After 200 hours, the yield may decrease to 35%. After 500 hours, the yield may be 30%. When this latter yield is reached, it may be necessary to reactivate or regenerate the catalyst.

This undesirable decrease in catalytic activity imposes an undesirable economic burden on the operation. Although these factors are noted with respect to the preferred process of transalkylation, comparable findings are observed in the case of other alkyl transfer type processes for treating alkylaromatic compositions at aromatic-ring-maintaining conditions such as isomerization, disproportionation, etc.

It is an object of this invention to provide a process for preparing aromatic hydrocarbons. It is another object of this invention to provide a process, such as a transalkylation process, characterized by increased catalyst life. Other objects of this invention will be apparent to those skilled in the art.

STATEMENT OF THE INVENTION

In accordance with certain of its aspects, the method of this invention for treating a charge stream containing (i) at least one alkylaromatic hydrocarbon having 6-12 carbon atoms and (ii) at least one hydrogen-deficient aromatic hydrocarbon having $(8+n)$ carbon atoms and less than $(10+2n)/(8+n)$ atoms of hydrogen per atom of carbon, wherein $n$ is an interger 0-8, may comprise hydrocracking said charge stream at aromatic-ring-maintaining conditions in the presence of hydrogen and at least one heterogeneous solid catalyst having a mole ratio of silica-to-alumina $SiO_2:Al_2O_3$ of 0-12:1, containing at least one metal selected from the group consisting of rhenium, Group VI B and Group VIII metals on acidic support, thereby converting said hydrogen-deficient aromatic hydrocarbon having less than $(10+2n)/(8+n)$ atoms of hydrogen per atom of carbon to more desirable aromatic hydrocarbons containing more hydrogen than said hydrogen-deficient hydrocarbons;

withdrawing from said hydrocracking operation a hydrocrackate stream containing (i) at least one alkylaromatic hydrocarbon having 6-12 carbon atoms and (ii) less than about 0.3 w% (based upon the total said product stream) of said hydrogen-deficient aromatic hydrocarbon having less than $(10+2n)/(8+n)$ atoms of hydrogen per atom of carbon wherein $n$ is an integer 0-8;

contacting said hydrocrackate stream, at aromatic-ring-maintaining alkyl-transfer conditions, with a heterogeneous solid alkyl transfer catalyst, having mole ratio of silica-to-alumina above about 12:1, and containing 0–10% of at least one Group VIII metal selected from the group consisting of nickel, cobalt, iron, platinum, palladium, rhodium, iridium, ruthenium, and osmium;

maintaining the content, in said hydrockate admitted to said contacting operation, of less than about 0.3% of said hydrogen-deficient aromatic compound thereby extending the effective life of said catalyst during said alkyl-transfer; and withdrawing product aromatic hydrocarbon from said alkyl transfer operation.

DESCRIPTION OF THE INVENTION

The charge stock which may be treated by the process of this invention may be an alkylaromatic hydrocarbon stream containing components having typically 6–12 carbon atoms. These streams may be recovered from a variety of sources including coal, tar sands, or from petroleum processes. They may, for example, be recovered as by-products from coke production, i.e., from the various distillate fractions. They may be produced during the processing of tar sands. They may be obtained as products or by-products during petroleum processing. At some time during processing, they will normally have been treated to lower their nitrogen (including organic nitrogen) content to below about 10 ppm, preferably to below about 1 ppm.

Depending on the further processing (i.e., transalkylation, disproportionation, isomerization, etc.) which is to be carried out, the streams so obtained may be further treated, as by fractionation, etc., to produce an alkylaromatic stream containing higher or lower proportions of selected components. For example, if it be desired to effect disproportionation or isomerization, then (subject to economic balance and the product to be prepared) the stream may be fractionated to narrow down the spread of the components; and in certain instances it may be desirable to fractionate the stream to contain, e.g., pure toluene or pure xylene(s). If on the other hand it is to be transalkylated, then initial treatment may be such as to yield a stream containing a wider range of components; and in certain instances it may be desirable to prepare a stream containing two pure components such as benzene and xylene(s).

Since the preferred process with which the instant invention may be useful is transalkylation, reference will hereinafter generally be made to that process. It will be apparent, however, from the description that comparable steps may be present when the process is disproportionation, isomerization, or other alkyl transfer-type reactions.

In one preferred transalkylation embodiment, the charge stock may be prepared typically the extracting aromatic components from the effluent from a reforming operation.

The feed to a reforming operation, typically a catalytic reforming operation, may be a naphtha, preferably a straight run naphtha such as a full boiling range naphtha derived from atmospheric pressure distillation of crude oil in a crude topping unit.

Typically a feed naphtha stream may be characterized by the following illustrative criteria:

| Property | Broad Range | Typical |
|---|---|---|
| API Gravity | 45–75 | 62 |
| IBP, °F | 40–150 | 100 |
| EBP, °F | 225–400 | 350 |
| RON, Clear | 30–70 | 56 |
| Aromatics, vol. % | 0–90 | 5 |
| Naphthenes, vol. % | 0–90 | 40 |
| Paraffins, vol. % | 3–90 | 55 |
| Olefins, vol. % | 0–50 | 0 |

In a preferred embodiment, the feed naphtha may be passed to a reforming operation, preferably a catalytic reforming operation, wherein reforming is carried out at 850° F.–975° F., say 940° F., at 0–800 psig, say 300 psig, with a WHSV of 1.0–10, say 2.8, and a hydrogen-to-hydrocarbon mole ratio of 2–10, say 7. The preferred catalyst may be, e.g., a noble metal on alumina, typically 0.6 wt. % platinum on alumina.

Reformate may be characterized by the following criteria:

| Property | Broad Range | Typical |
|---|---|---|
| API Gravity | 35–60 | 45 |
| IBP, °F | 80–150 | 110 |
| EBP, °F | 350–425 | 410 |
| RON, Clear | 80–105 | 93 |
| Aromatics, vol. % | 30–70 | 58 |
| Naphthenes, vol. % | 0–20 | 4 |
| Paraffins, vol. % | 5–60 | 38 |
| Olefins, vol. % | 0–5 | 0 |

The reformate is passed to a separation operation, preferably a solvent extraction operation, typically a Udex unit, wherein aromatics may be separated from nonaromatics. Reformate may, for example, be contacted with aqueous glycols to permit attainment of aromatic extract characterized by the following criteria;

| Property | Broad Range | Typical |
|---|---|---|
| API Gravity | 30–60 | 33 |
| IBP, °F | 80–150 | 176 |
| EBP, °F | 250–350 | 410 |
| Aromatics, vol. % | 90–100 | 98 |
| Naphthenes, vol. % | 0–5 | 1 |
| Paraffins, vol. % | 0–10 | 1 |
| Olefins, vol. % | 0–5 | 0 |

Although such a charge aromatic stream containing $C_6$ to $C_{11}$ aromatics may be typical of those which may be treated by the preferred process of this invention, other streams containing alkylbenzenes having 6–12 carbon atoms may be employed — such as those characterized by the following criteria:

| Components | Broad Wt. % |
|---|---|
| Benzene | 0–50 |
| Toluene | 0–50 |
| Xylenes | 0–100 |
| $C_9$ aromatics | 0–100 |
| $C_{11}$ | 0–80 |
| $C_{12}$ | 0–50 |

It will be apparent for example that a charge stream may for example contain 100% of isodurene, or 100% of xylenes, or 100% of pseudocumene, or 100% of ethylxylenes, etc. or it may contain mixtures of any of those with toluene or benzene. Still another typical charge stream which may be treated by the process of this invention to produce xylene may be referred to as a crude xylene stream containing typically the following:

| Component | Broad Wt. % | Typical Wt. % |
|---|---|---|
| Benzene | 0–2 | 0.5 |
| Toluene | 0–10 | 2.5 |
| Xylenes | 70–100 | 84.4 |
| Ethylbenzene | 0–20 | 9 |
| $C_9$ aromatics | 0–10 | 3.5 |

-continued

| Component | Broad Wt. % | Typical Wt. % |
|---|---|---|
| Other | 0–5 | 0.1 |

The major components of the charge stream are monocyclic alkylaromatic hydrocarbons which are free on any non-aromatic unsaturation and, more particularly, are free of any ethylenic (including non-aromatic double or triple bonds) unsaturation. More particularly, these compounds are characterized by the formula $C_{6+m}H_{6+2m}$ wherein $m$ is an integer 0–10, preferably 0–6.

Typical of these compounds are those noted in the following table:

TABLE

| m | Formula | Typical Compounds |
|---|---|---|
| 0 | $C_6H_6$ | benzene |
| 1 | $C_7H_8$ | toluene |
| 2 | $C_8H_{10}$ | xylenes |
|   |   | ethyl benzene |
| 3 | $C_9H_{12}$ | trimethyl benzenes |
|   |   | ethyl toluenes |
|   |   | cumene |
|   |   | n-propyl benzene |
| 4 | $C_{10}H_{14}$ | tetramethyl benzenes |
|   |   | diethyl benzenes |
|   |   | ethyl xylenes |
|   |   | cymenes cymenes |
|   |   | butyl benzenes |
| 5 | $C_{11}H_{16}$ | pentamethyl benzene |
|   |   | ethyl trimethyl benzenes |
|   |   | diethyl toluenes |
|   |   | propyl xylenes |
|   |   | propyl ethyl benzenes |
| 6 | $C_{12}H_{18}$ | hexamethyl benzene |
|   |   | ethyl tetramethyl benzenes |
|   |   | diethyl xylenes |
|   |   | triethyl benzenes |
|   |   | dipropyl benzenes |

In addition to the noted major components of the charge streams, it is found that they also contain undesired species. It has been found that these undesired species are characterized by the fact that they contain $8+n$ carbon atoms and less hydrogen than is present in the compounds having the formula $C_{8+n}H_{10+2n}$ wherein $n$ is an integer 0–8, preferably 0–4. Expressed alternatively, the hydrogen content of these undesired species is such that these compounds have less than $(10+2n)/(8+n)$ atoms of hydrogen per atom of carbon.

Typical of the undesired hydrogen-deficient aromatic species are those noted in the following table:

TABLE

| n | Formula | Typical Compounds |
|---|---|---|
| 0 | $C_8H_8$ | styrene |
| 1 | $C_9H_{10}$ | methyl styrene |
|   | " | indan |
|   | $C_9H_8$ | indene |
| 2 | $C_{10}H_{12}$ | butenyl benzene |
|   | " | ethyl styrene |
|   | " | methyl indan |
|   | $C_{10}H_{10}$ | methyl indene |
|   | $C_{10}H_8$ | naphthalene |
| 3 | $C_{11}H_{14}$ | pentenyl benzene |
|   | " | trimethyl styrene |
|   | " | ethyl indan |
|   | " | dimethyl indans |
|   | $C_{11}H_{12}$ | dimethyl indenes |
|   | $C_{11}H_{10}$ | methyl naphthalenes |
| 4 | $C_{12}H_{14}$ | dimethyl naphthalenes |
| 6 | $C_{14}H_{10}$ | anthracene |
|   |   | etc. |

While all of these hydrogen deficient species are undesirable because they promote deterioration of the catalyst, it is found that those species more deficient in hydrogen, e.g. naphthalene, promote deterioration at a faster rate than less hydrogen-deficient species, e.g. methyl indane.

Some of these undesirable compounds may be characterized as fused polycyclic, typically dicyclic, hydrocarbons commonly containing at least one aromatic ring.

Illustrative of these fused polycyclic hydrocarbons may be noted the following:

| Compound | Boiling Point ° F |
|---|---|
| Naphthalene | 424 |
| Methyl-naphthalenes | 466–471 |
| Dimethyl-naphthalenes | 514 |
| Indane | 352 |
| Indene | 361 |
| Anthracene | 640 |

It may be noted that, although many (in terms of species and/or quantity) of these undesirable compounds may possess a boiling point above that of the heaviest component (e.g. xylene or $C_9$) normally present in significant quantities in the, e.g., $C_6$–$C_9$ charge, there may normally be at least some portion of these compounds present in the charge which may have a boiling point close to or below that of the heavier monocyclic alkylaromatic hydrocarbon component — typically xylene, $C_9$, or $C_{10}$.

The total content of undesirable "hydrocarbon-deficient" species may preferably be present in the charge streams to alkyl transfer (i.e., transalkylation, isomerization or disproportionation) in amount of 0%–0.3%, preferably 0%–0.2%, say less than about 0.1%, of the total charge stream.

In practice of one aspect of the process of this invention, the charge stream to hydrocracking operation contains (i) a lighter monocyclic aromatic hydrocarbon component, typically benzene, (ii) a heavier monocyclic alkylaromatic hydrocarbon component, typically xylenes, and (iii) 0.3%–10% of the undesired hydrogen-deficient component. The charge stream (or preferably the components prior to blending) is hydrocracked to decrease the content of undesirable hydrocarbons to less than about 0.3%, preferably to 0%–0.2%, typically 0%–0.1%, say at about 0.1% or less based on the weight of undesired hydrogen-deficient component in the total charge stream.

Hydrocracking of the charge stream containing (i) at least one alkylaromatic hydrocarbon having 6–12 carbon atoms and (ii) at least one hydrogen-deficient aromatic hydrocarbon having less than $(10+2n)/(8+n)$ atoms of hydrogen per atom of carbon wherein $n$ is an integer 0–8, at aromatic ring maintaining conditions in the presence of hydrogen and at least one heterogeneous solid catalyst containing Group VIII metal on acidic support thereby converts said hydrogen-deficient aromatic hydrocarbons having less than $(10+2n)/(8+n)$ atoms of hydrogen per atom of carbon to aromatic hydrocarbons containing more hydrogen than said hydrogen-deficient hydrocarbons.

Hydrocracking the charge stream may be typically effected at 400° F.–900° F., preferably 500° F.–800° F., say 700° F. at 50–2000 psig, preferably 200–1000 psig, say 750 psig at LHSV of 0.2–10, say 1, and hydrogen to hydrocarbon mole ratio of 2–20, say 5:1. Sulfur may be present in mole ratio of $H_2$:$H_2S$ of 20:1–2000:1, say 200:1.

Hydrocracking may be preferably carried out in vapor phase over a heterogeneous catalyst which contains (i) a support and (ii) at least one metal selected from the group consisting of rhenium, Group VI B, and Group VIII metals. The heterogeneous solid catalyst is characterized by its moderate cracking ability, high hydrogenation ability, and by moderate acidity. The support is particularly characterized by a low mole ratio fo silica-to-alumina. The preferred low ratio may be 0-12, say 3-8. It will be apparent that an alumina (which contains no silica) is characterized by a mole ratio of 0. Preferably the catalyst is sulfided and hydrocracking is effected preferably in the presence of carbon disulfide or more preferably hydrogen sulfide.

The catalyst may be (i) an alumina — such as gamma alumina — mole ratio of zero; (ii) a fluorided alumina containing 1%-10%, say 3%-6% fluoride — mole ratio of zero; (iii) an acidic silica-alumina having a mole ratio of 3; (iv) a Group VIII metal plus a Group VI B metal deposited on a zeolite X which has been exchanged with a rare earth or a Group II B metal — mole ratio 2.5 (v) a hydrogen form zeolite Y — mole ratio 8 — which has been impregnated with a Group VIII metal; (vi) a rare earth exchanged zeolite Y — mole ratio 8 — which has been impregnated with a Group VIII metal; etc.

Illustrative specific preferred catalysts may be the following:

| (i) | 92 wt % | gamma alumina |
| --- | --- | --- |
|  | 3 wt % | fluorine |
|  | 5 wt % | cobalt sulfide | having a silica-to-alumina ratio of zero;

| (ii) | 88 wt % | kaolin matrix |
| --- | --- | --- |
|  | 11.25 wt % | rare earth exchanged zeolite Y |
|  | 0.75 wt % | palladium | having a silica-to-alumina ratio of 5

| (iii) | 55 wt % | silica-alumina matrix |
| --- | --- | --- |
|  | 6 wt % | nickel |
|  | 19 wt % | tungsten |
|  | 5 wt % | sulfide |
|  | 15 wt % | ultrastable zeolite Y | having a silica-to-alumina ratio of 8

Preferred charge to hydrocracking includes hydrocarbon, 2000-20,000 SCFB, say 5000 SCFB of hydrogen, and 1-1,000 SCFB, say 25 SCFB of hydrogen sulfide — total LHSV is 0.3-5 say 1 based upon the empty reactor.

During hydrocracking under the noted conditions, the aromatic rings in the alkylaromatic charge may be neither hydrogenated nor cracked to any significant degree. It is however a feature of the process of this invention that the hydrogen deficient hydrocarbons may, under the conditions of reaction be cracked, hydrogenated, or both. In the case of eg styrene in the charge, it may be hydrogenated to ethylbenzene and/or cracked to give benzene and eg ethane. In the case of eg indene for example, it may be hydrocracked to form a product containing toluene and xylene.

In general it may be said that the content of the hydrogen deficient species, which in the charge may be as high as 5% (or even higher depending on the particular source and/or make-up of the charge) may be lowered during hydrocracking to 0-0.3 w % preferably 0-0.2 w % say less than about 0.1 w %.

Specifically in the case of particular compounds, the ratio of atoms of hydrogen per atom of carbon may be increased toward the value $(10+2n)/(8+n)$. In the typical case of styrene which is hydrogenated to ethylbenzene, the ratio may increase from 1 up to 1.25.

The hydrocrackate may be withdrawn from the hydrocracking operation and fractionated to separate desired fractions prior to further processing. Alternatively there may be added to or withdrawn from hydrocrackate additional quantities or components to maximize efficiency of subsequent operations. For example if the hydrocrackate is to be transalkylated, benzene may be added to or withdrawn from the hydrocrackate or alternatively xylenes or $C_9$ may be added to or withdrawn from the hydrocrackate.

It is a particular feature of this invention according to its preferred aspects that no fractionation, addition, or withdrawal of hydrocarbon need be effected; but the hydrocrackate may be passed directly to alkyl transfer.

The hydrocrackate charge stream, which may serve as a charge monocyclic alkylaromatic hydrocarbon stream to the transalkylation operation to make xylenes may in one preferred embodiment be a toluene-trimethylbenzene stream substantially free of undesirable hydrogen-deficient hydrocarbon components and may typically have the following compositions:

TABLE

| Component | Broad | Typical |
| --- | --- | --- |
| Benzene | 0-10 | 0.3 |
| Toluene | 30-50 | 37.4 |
| Xylenes | 0-20 | 1.2 |
| Trimethylbenzenes | 45-75 | 61.0 |
| Undesirables (e.g. indan) | 0-0.5 | 0.1 |

In the practice of the preferred aspects of the process of this invention, the charge to transalkylation will contain less than about 0.3 wt % of hydrogen deficient hydrocarbons based on the total charge.

Transalkylation may be carried out at aromatic-ring maintaining conditions of temperature, pressure, etc. in the presence of a transalkylation catalyst. Transalkylation is preferably effected at 500° F.-800° F. (i.e., 260° C.-427° C.), more preferably 350° F.-750° F. (i.e., 288° C.-399° C.), say 650° F. (i.e., 343° C.) and 100-2000 psig, preferably 300-1000 psig, say 800 psig at LHSV of 1-15, say 4 and H$_2$:H$_2$S mole ratio of 50-1000:1, preferably about 200:1.

Transalkylation catalyst may include a heterogenous solid alkyl transfer catalyst characterized by weak hydrogenation ability and by strong acidity. It is particularly characterized by a high mole ratio of silica-to-alumina SiO$_2$:Al$_2$O$_3$. The preferred high ratio may be above about 12:1 and as high as about 200:1. Typically the ratio may be 30-60:1, say 40:1.

One preferred high ratio acid catalyst may be an acid leached clinoptilolite as disclosed in U.S. Pat. No. 3,565,788. Another preferred catalyst may be an acid leached or hydrogen mordenite which may optically (and preferably) bear a Group VIII metal thereon. Such high ratio acid mordenites may be disclosed in U.S. Pat. Nos. 3,476,821 or 3,780,121 or 3,780,123. Other illustrative high ratio catalysts may include high ratio heulandite, ultrastable high ratio forms of faujasite, etc. The high ratio catalysts may preferably bear a Group VIII metal thereon.

Illustrative specific preferred high ratio catalysts may be the following:

| (i) | 80.6 wt % | acid leached hydrogen mordenite (silica-to-alumina mole ratio 40:1) |
|---|---|---|
| | 4.4 wt % | cobalt |
| | 15 wt % | gamma alumina | this catalyst being sulfided prior to use — prepared by the process of Example I of U.S. Pat. No. 3,780,123;

| (ii) | 74.9 wt % | acid leached hydrogen mordenite (silica-to-alumina mole ratio 60:1) |
|---|---|---|
| | 4.6 wt % | nickel |
| | 5.5 wt % | sulfur |
| | 15 wt % | gamma alumina | this catalyst being sulfided prior to use — prepared by the process of Example II of U.S. Pat. No. 3,780,123;

| (iii) | 77.6 wt % | acid leached hydrogen mordenite (silica-to-alumina mole ratio 16:1) |
|---|---|---|
| | 4.7 wt % | cobalt |
| | 2.7 wt % | sulfur |
| | 15 wt % | gamma alumina | this catalyst being sulfided prior to use — prepared by the process of Example III of U.S. Pat. No. 3,780,123;

| (iv) | 91.1 wt % | acid leached hydrogen mordenite (silica-to-alumina mole ratio 65:1) |
|---|---|---|
| | 5.5 wt % | cobalt |
| | 3.4 wt % | sulfur | this catalyst being sulfided prior to use — prepared by the process of Example IV of U.S. Pat. No. 3,780,123;

| (v) | 98 wt % | acid leached hydrogen mordenite (silica-to-alumina mole ratio 18.1:1) |
|---|---|---|
| | 2 wt % | sulfur |

— prepared by the process of Example I of U.S. Pat. No. 3,780,121;

| (vi) | 80 wt % | acid leached hydrogen mordenite (silica-to-alumina mole ratio 40:1) |
|---|---|---|
| | 15 wt % | gamma alumin |
| | 5 wt % | CuO . Cu $Cr_2O_4$ |

— prepared by the process of Example II of U.S. Pat. No. 3,780,121.

| (vii) | 99.52 wt % | acid leached clinoptilolite (silica-to-alunina mole ratio 40:1) |
|---|---|---|
| | 0.48 wt % | palladium |

— prepared by the process of Example III of U.S. Pat. No. 3,565,788.

One preferred catalyst may include (a) 15% of alumina matrix, and (b) 85% of 7% cobalt sulfide on 40:1 $SiO_2:Al_2O_3$ acid-leached mordenite. 0.5% sulfur (as $H_2S$) is present in the hydrogen stream.

In order to maintain aromatic ring-retaining conditions, these metals should be sulfided and a sulfide, eg hydrogen sulfide or a hydrogen sulfide precursor ($H_2/H_2S$ mole ratio of 20 to 2000:1) be included in the feed stream.

Transalkylate of the above stream may typically contain the following:

TABLE

| Component | Broad | Typical |
|---|---|---|
| Benzene | 0–10 | 2.5 |
| Toluene | 15–30 | 19.5 |
| Xylenes | 5–42 | 40 |
| Trimethylbenzenes | 25–50 | 29 |
| Tetramethylbenzenes & heavier | 0–15 | 9.0 |

It is a feature of this invention that transalkylation may be carried out for extended times at high levels without regeneration. Typically, for example, such operations may permit catalysts to have useful half-lives of more than 2 to 20 times the half life of catalyst when the feedstock is not so treated (the useful half-life is defined as the time for the conversion to decrease to one-half of the initial lined-out value).

It has heretofore been observed that the initial, lined out yield in transalkylation reactions such as making xylenes may typically be about 40%. (it will be apparent to those skilled in the art that this yield may vary depending on the conditions of operation including temperature, pressure, catalyst species, space velocity, etc.). After 200 hours, the yield may decrease to eg 35%; and at 500 hours, the yield may be about 25%.

Practice of the process of this invention permits alkyl transfer, such as transalkylation, isomerization, disproportionation, etc., to be carried out with little or no decrease in activity or yield for periods of 100–200 hours or longer; and decreases noted during or after this period are less than occur in the prior art.

Maintenance of the content of polycyclic fused hydrocarbons below 0.3% permits attainment of unexpected advantages. For example, with a typical transalkylation catalyst of the acid mordenite type (operating at about 2 LHSV) and 600° F., the useful half-life as a function of content of an illustrative hydrogen deficient hydrocarbon may be as follows:

| Naphthalene Content | Half-Life |
|---|---|
| 1% | 10 hours or less |
| 0.3% | 24 hours |
| 0.1% | 100 hours |
| 0.005% | over 300 hours |

In typical commercial operation, it may be found that the novel technique of this invention permits increase in the useful period (during which a catalyst may be used prior to regeneration) by a factor of 2 to 20 typically 5.

It is also found that continuing operation may be carried out at lower temperature. Prior commercial practice may include the use of higher temperature as the catalyst is rendered less operative by the build-up of undesirables such as carbon, resinous material, etc.

It may also be found that regeneration may be carried out at lower temperatures for shorter time; and the catalyst may be regenerated for many more cycles before it must be discarded.

Results comparable to those noted for transalkylation processes may be achieved by decreasing, to less than 0.3%, the content of hydrogen-deficient components in a charge stream of trimethylbenzenes or of tetramethylbenzenes of an isomerization operation carried out at 800° F.–1100° F., preferably 850° F.–1000° F., say 920° F., and 50–1500 psig, preferably 150–1000 psig, say 300 psig, and LHSV of 0.2–5, preferably 0.5–2, say 1, over acid leached clinoptilolite (ratio 40:1) bearing 0.5% palladium. In this instance the half-life of the catalyst may be increased by as much as three times.

Similarly comparable results, in terms of extended catalyst half-life, may be attained in disproportionation processes carried out at 500° F.–800° F., preferably 550° F.–750° F., say 620° F., and 100–1500 psig, preferably 300–1000 psig, say 800 psig, over a catalyst containing 7% CoS on 40:1 $SiO_2:Al_2O_3$ acid-leached mordenite dispersed in 15% alumina matrix.

It appears that the undesirable aromatic hydrocarbons which are removed in practice of the process of this invention are particularly undesirable in that, inter alia, they may lay down on the catalyst a resinous or polymeric deposit (including that formed by reactions of the double bonds in many of these materials, and this deposit is peculiarly able to decrease the activity of the catalyst.

The compounds which are to be removed in practice of this invention are not primarily characterized by boiling point. For example, indane b.p. 349° F. (175.6° C.), and indene b.p. 361° F. (182.4° C.), possess boiling points lower than, e.g., iso-durene (1,2,3,5-tetramethyl benzene) (b.p. 388° F. (198° C.) the latter compound being an innocuous component in the conversion of $C_{10}$ streams by disproportionating isomerization, or transalkylation.

It is also a feature of the process of this invention that it permits more controlled operation. In prior practice, as the catalyst becomes spent, it has been common practice to increase the temperature of operation in an attempt to maintain the desired yield. Although this may raise the conversion to (or, more accurately, maintain it at) desired predetermined levels, this may change the selectivity of desired product — aside from the economically undesirable aspects of the higher temperature level. Use of the novel process of this invention permits one to operate for longer periods of time at one temperature (with attainment of substantially constant yield) or, alternatively, to increase the temperature by a lesser degree as the catalyst activity decreases.

Another advantage which might accrue by practice of the process of this invention is that the catalyst may have a longer life prior to the point at which it must be discarded. Even though care is exercised in regenerating catalyst, upsets can happen which shorten catalyst life during regeneration. On average a catalyst can be regenerated only a limited number of times before it must be discarded. Longer periods of operation between regeneration thus extend the ultimate useful life of the catalyst.

PRACTICE OF PREFERRED EMBODIMENT

Practice of the process of this invention may be apparent to those skilled in the art from the following wherein, as elsewhere in this specification, all parts are parts by weight unless otherwise specified.

EXAMPLE I

A mixture of 42.0% benzene, 0.2% toluene, 0.49% styrene, 4.5% ethyl benzene and 52.9% mixed xylenes is transalkylated in a control run over a 40:1 $SiO_2:Al_2O_3$ acid-leached mordenite dispersed in 15% alumina matrix at 300 psig, 600° F., 2 LHSV and a hydrogen rate of 7,000 SCFB of liquid feed.

| The initial product contains | |
|---|---|
| Light gases | 0.5% |
| Benzene | 29.5 |
| Toluene | 34.6 |
| Ethyl benzene | 2.8 |
| Mixed xylenes | 26.0 |
| Ethyl toluenes | 1.8 |
| Trimethyl benzenes | 4.2 |
| Ethyl xylenes | 0.5 |
| Tetramethyl benzenes | 0.1 |
| | 100.0% |

However, after a period of 100 hours on stream in a control run, the conversion to toluene drops to 29%.

In an experimental run, the charge may be hydrocracked at 520° F. and 750 psig at LHSV of 1.0, hydrogen content of 5000 SCFB, and hydrogen sulfide content of 25 SCFB over 5% cobalt sulfide on an alumina containing 3% fluorine. The styrene content is thus lowered to less than 0.1 w %. The hydrocrackate is directly transalkylated as in the control. As judged by toluene formation, the activity of the catalyst is maintained over the 100 hour time span.

EXAMPLE II

Pseudocumene (containing 0.35% alpha methylstyrene and 0.2% sulfide present as methyl disulfide) is isomerised and disproportionated over a catalyst (similar to the transalkylation catalyst of Example I) at 2.0 LHSV, 550° F., 300 psig, 5000 SCFB of hydrogen.

The initial product (formed after 6 hours on stream needed to line out the unit to a steady-state operation) is as follows in this control run:

| Material | GC* Area Percent | Disproportionation Equilibrium Product in Volume Percent |
|---|---|---|
| Light paraffins ($C_5$) | 0.6 | — |
| Naphthenes ($C_6$–$C_8$) | trace | — |
| Benzene | 0.1 | 0.2 |
| Toluene | 2.1 | 3.8 |
| Xylenes | 16.9 | 22.0 |
| Ethyl toluenes | 0.1 | — |
| Mesitylene | 14.2 | 10.1 |
| Pseudocumene | 37.6 | 26.4 |
| Hemimellitene | 4.6 | 2.7 |
| Ethyl xylenes | 0.4 | — |
| Durene | 8.6 | 10.9 |
| Isodurene | 12.3 | 15.9 |
| Prehnitene | 2.2 | 4.3 |
| Ethyl $C_{11}$ aromatics | 0.2 | — |
| Pentamethyl benzene | trace | 3.7 |

*GC = gas chromatographic analysis

If complete disproportionation-isomerization equilibrium were attained, only 39.2% of the feed would be retained as trimethyl benzenes. Of the $C_9$ aromatics cut, 25.8% would be mesitylene. At 100% disproportionation equilibrium, 31.1% tetramethyl benzenes would be formed.

It is seen that the initial activity is such that over 43% of the feed is disproportionated, forming 23.1% tetramethyl benzenes. Of the 56.4% of the feed remaining as trimethyl benzenes, 25.2% of this $C_9$ cut is present as mesitylene. Thus, the catalyst is a good disproportionation-isomerization catalyst and an excellent (close to equilibrium) isomerization catalyst.

With 24 hours of being on stream in this control run with the feed containing alpha methylstyrene, the amount of product disproportionated drops from 23.1% to 14.6%. Furthermore, the approach to equilibrium for the isomerization of the pseudocumene to mesitylene drops from about 97% to about 70%.

In an experimental run, the charge pseudocumene is hydrocracked at 550° F. and 750 psig at LHSV of 2, hydrogen content of 5000 SCFB, and hydrogen sulfide content of 10 SCFB over 5% nickel sulfide on alumina (fluorided with 4% fluoride and thereafter calcined). The content of alpha methyl styrene is lowered to about 0.08 w % in the hydrocrackate.

This hydrocrackate is passed directly to disproportionation. The yield of tetramethyl benzenes, as formed by disproportionation remains above 20% over the 24-hour period; and the amount of mesitylene formed by isomerization of the pseudocumene remains above 90% of the theoretical equilibrium amount (which is 25.8% of the trimethyl benzene fraction).

EXAMPLE III

A nominal 330°-350° F. boiling fraction from a solvent extract of catalytic reformate contains the following:

|  | Weight % |
|---|---|
| Paraffins and naphthenes | 0.2 |
| Ethyl toluenes | 16.5 |
| Trimethyl benzenes | 82.2 |
| Cymenes | 0.3 |
| Indan | 0.8 |
|  | 100.0 |

59 parts of volume toluene are mixed with 70 parts by volume of the 330°-350° F. fraction to form a charge mixture containing 0.43% indan. This mixture is then transalkylated (in a control run) over 7% CoS on acid-leached mordenite catalyst (ratio of silica-to-alumina of 60) at 2 LHSV, 5000 SCFB hydrogen, at 550° F. and 800 psig. The initial product (after 6 hours) contains:

|  | Weight % |
|---|---|
| Cracked products ($C_2$-$C_6$) and $C_6$-$C_7$ naphthenes | 0.90 |
| Benzene | 3.69 |
| Toluene | 22.75 |
| Ethyl benzene | 1.17 |
| Xylenes | 36.15 |
| Ethyl toluenes | 6.03 |
| Trimethyl benzenes | 22.12 |
| Cymenes | 0.18 |
| Ethyl xylenes | 3.78 |
| Tetramethyl benzenes | 2.96 |
| $C_{11}$ and heavier | 0.27 |
|  | 100.00 |

It is seen that about 37.3% $C_8$ aromatics are formed by the transalkylation reaction.

After 24 hours the activity of the catalyst declines so that only 26% $C_8$ aromatics are produced in this control run. The spent catalyst contains 3.7% carbon after all volatiles are stripped off in a stream of nitrogen at 500° F.

In an experimental run, the same 330° F.-350° F. boiling fraction from a solvent extract of catalytic reformate containing 0.8 w % indan is hydrocracked at 700° F. and 750 psig, LHSV of 1, hydrogen to hydrocarbon mole ratio of 6:1, and hydrogen to $H_2S$ mole ratio of 250:1. Hydrocracking catalyst is 88% of a kaolin matrix containing 11.25 w % of rare earth exchanged zeolite Y bearing 0.75% palladium — having a silica-to-alumina mole ratio of 5. The hydrocrackate may contain:

|  | Weight % |
|---|---|
| Ethyl toluenes | 18.2 |
| Trimethyl benzenes | 81.5 |
| Paraffins and naphthenes | 0.22 |
| Indan | 0.08 |

Six volumes of this stock are blended with 5 volumes of toluene, 0.2% sulfide is added as methyl disulfide. The mixture contains less than 0.05% indan. The mixture is transalkylated at the same conditions as above, namely 550° F., 800 psig, 1 LHSV, 5000 SCFB hydrogen. Catalyst is acid leached mordenite (having silica-to-alumina mole ratio of 60) plus 7% CoS. The product formed is:

|  | Weight % |
|---|---|
| Cracked and naphthenes | 0.91 |
| Benzene | 3.62 |
| Toluene | 22.57 |
| Ethyl benzene | 1.18 |
| Xylenes | 36.26 |
| Ethyl toluenes | 6.07 |
| Trimethyl benzenes | 22.48 |
| Diethyl benzenes | 0.09 |
| Ethyl xylenes | 3.72 |
| Tetramethyl benzenes | 2.99 |
| $C_{11}$ and heavier | 0.99 |

About 38.4% $C_8$ aromatics are formed and, after 24 hours on stream, the system continues to form about 35% $C_8$ aromatics in this experimental run.

In contrast, the feed containing the 0.43 wt. % indan of the control causes catalyst deactivation. It is seen then that the presence of indan is detrimental to catalyst life and feeds should be treated so that they contain less than 0.3%, preferably less than 0.1% indan.

SUMMARY

Example I — Styrene, $C_8H_8$, has less hydrogen than the required amount ($C_8H_{10}$); hence, it promotes more rapid catalyst aging. Removal of styrene by hydrocracking permits transalkylation to be carried out over 100 hours with no decrease in conversion. Control run gives decrease to 39/34.4 or 84%.

Example II — Methylstyrene present in a disproportionation operation cuts yield (after 24 hours) from 23.1% to 14.6%. Removal of methylstyrene by hydrocracking permits disproportionation yield to be maintained above 20%. Similar treatment of charge permits isomerization yield to remain above 90% rather than dropping to 70% as in control.

Example III — Indane removal by hydrocracking permits transalkylation catalyst to continue at high yield in contrast to control runs wherein yield dropped to 26/37.3 or 70%.

EXAMPLE IV

A vacuum gas oil, 28.9°API gravity, 0.2% sulfur, 111 ppm total nitrogen and with 10, 50, and 90% boiling overhead at 596, 710, and 786° F. is catalytically cracked over an equilibrium cracking catalyst formed from a rare earth exchanged zeolite Y dispersed in a kaolin matrix, at a reactor temperature of 1097° F., with a weight hourly space velocity of 1.56 and a catalyst to charge oil ratio of 6.75. The product formed, in wt % is:

| | |
|---|---|
| Hydrogen | 0.47 |

-continued

| | |
|---|---|
| Methane | 5.54 |
| Ethylene | 3.20 |
| Ethane | 2.44 |
| $C_3$'s | 16.72 |
| $C_4$'s | 17.98 |
| $C_5$'s | 3.59 |
| 115–410° F Naphtha | 25.79 |
| 410–670° F Gas Oil | 14.70 |
| 670+° F Gas Oil | 3.48 |
| Coke | 6.08 |

With a total conversion of 84% to material boiling below the initial boiling point of the feedstock.

Analysis of the naphtha indicates it to contain:

| | Wt % |
|---|---|
| Nonaromatics boiling below benzene | 6.32 |
| Nonaromatics boiling above benzene | 10.65 |
| Benzene | 4.01 |
| Toluene | 25.51 |
| Ethylbenzene | 3.38 |
| Xylenes | 24.40 |
| n-propylbenzene | 0.56 |
| ethyl toluenes | 6.54 |
| trimethylbenzenes | 11.29 |
| indan | 0.58 |
| n-propyl toluenes | 0.54 |
| diethylbenzenes | 1.78 |
| ethylxylenes | 1.41 |
| tetramethylbenzenes | 0.84 |
| methyl indans | 0.36 |
| naphthalene | 0.62 |
| $C_{11}$ aromatics | 0.21 |

Isopropylaromatics such as cumene and cymenes and butylbenzenes (n, secondary, iso, tertiary) are not detected in the naphtha due to the relatively severe catalytic cracking conditions which effect their conversion to other products.

In order to provide improved engine warmup and uniform fuel distribution to all cylinders in engines meeting low hydrocarbon and carbon monoxide requirements, higher volatility fuels with narrower boiling ranges are being considered. These fuels may have end points of approximately 330° F. and the heavier components such as the higher boiling 15 percent portion of the catalytically cracked naphtha would not be blended into the narrower boiling gasoline. Since the 330+° F. fraction is virtually all aromatic, alkyl benzene transfer processes that can lower the boiling range without significant loss of liquid volume are of particular value in converting more of the total product into high octane components of the required boiling range. Aromatic dealkylation processes may be practiced but at considerable sacrifice in liquid volume.

Alkylbenzene transalkylation and disproportionation can be used to increase the < 330° F. fraction. However, the presence of the hydrogen deficient aromatics such as indan, methyl indans and naphthalene in the 330+° F. boiling fraction can cause rapid deactivation of the alkyl transfer catalysts.

In a particular embodiment of this disclosure the cracked naphtha is fractionated to provide an 80% overhead and bottoms containing mostly 330° F. and higher boiling fraction.

These bottoms contain 4 ppm nitrogen 320 ppm sulfur and the following aromatics:

| | Wt percent |
|---|---|
| xylenes | 0.2 |
| n-propylbenzene | 0.9 |
| ethyl toluenes | 21.4 |
| trimethylbenzenes | 49.3 |
| indan | 2.8 |
| n-propyltoluenes | 2.7 |
| diethylbenzenes | 9.2 |
| ethylxylenes | 7.1 |
| tetramethylbenzenes | 3.3 |
| methylindans | 1.1 |
| $C_{11}$ polyalkylbenzenes | 0.8 |
| naphthalene | 1.2 |

This stock contains a total of 5.1 weight percent of hydrogen deficient aromatic species including indan, methyl indans and naphthalene. About 35% boils below 330° F.

The 320°–410° F. naphtha is hydrocracked at 1500 psig, 780° F., 1 LHSV, 5000 SCFB hydrogen and 25 SCFB hydrogen sulfide over a sulfided (5%) catalyst containing 6 wt percent nickel, 19 weight percent tungsten dispersed on a support formed from 15 weight percent ultrastable Y zeolite (having a silica-to-alumina ratio of 8) dispersed in a 55% silica-alumina matrix. The liquid product contains:

| | Wt % |
|---|---|
| $C_3$–$C_5$ paraffins | 1.28 |
| benzene | 4.79 |
| toluene | 9.47 |
| ethylbenzene | 2.04 |
| xylenes | 3.62 |
| n-propylbenzene | 0.13 |
| ethyltoluenes | 15.36 |
| trimethylbenzenes | 49.13 |
| indan | 0.12 |
| n-propyltoluenes | 0.13 |
| diethylbenzenes | 4.51 |
| ethylxylenes | 4.27 |
| tetramethylbenzenes | 4.56 |
| methylindans | 0.08 |
| $C_{11}$ polyalkylbenzenes | 0.50 |

After hydrocracking, the amount of material boiling below 330° F. is approximately 50 percent. Hydrocracking reduces the polynuclear aromatic or hydrogen deficient aromatic species to a total concentration of 0.2 weight percent. Hydrocracking also reduces the concentrations of n-propyl-benzene and n-propyl toluenes which can be precursors of indan and methyl indans under dehydrogenative conditions.

Hydrocracking removes the organic nitrogen and oxygenates (including dissolved molecular oxygen) from the feedstock as ammonia and water. These materials in small quantities (<10 ppm $NH_3$, <0.15 psia $H_2O$) are not harmful to mordenite alkyl transfer reaction catalyst. However, should higher concentrations prevail, it is desirable to remove these impurities such as by cooling and condensing the hydrocarbons and venting the impurities in the gas phase.

When the above hydrocracked product is cooled to 600° F. and depressurized to 600 psig and disproportionated over a cobalt (4.7%) sulfide (2.7%) on acid leached mordenite 77.6% (silica-to-alumina mole ratio of 16) dispersed in 15% of a gamma alumina matrix at 2.5 LHSV, the composition of the liquid product after 48 hours, is after stabilization at 150° F.

| | Weight % |
|---|---|
| Light paraffin ($C_5$–$C_7$) | 0.70 |
| Benzene | 2.91 |
| Toluene | 10.23 |
| Ethylbenzene | 1.70 |
| xylenes | 26.22 |

| | Weight % |
|---|---|
| n-propylbenzene | 0.04 |
| ethyl toluenes | 8.77 |
| trimethylbenzenes | 20.92 |
| n-propyl toluenes | 0.07 |
| diethyl benzenes | 0.56 |
| ethylxylenes | 14.76 |
| tetramethylbenzenes | 5.80 |
| $C_{11}$ and heavier polyalkylbenzenes | 7.32 |

Approximately 56 percent of the disproportionated product boils below 330° F.

A higher yield of product boiling below 330° F. is obtained by adding 100 parts by volume of a mixture of 12 percent benzene and 88 percent toluene obtained from topping (fractionating) the transalkylation product plus makeup toluene to 100 parts of the hydrocrackate and transalkylating under the same conditions as used for disproportionating the hydrocrackate. The product after 48 hours contains:

| | |
|---|---|
| non-aromatics ($C_5$–$C_7$) | 1.70 |
| benzene | 21.14 |
| toluene | 62.49 |
| ethylbenzene | 6.43 |
| xylenes | 58.54 |
| n-propylebenzene | 0.05 |
| ethyl toluenes | 14.52 |
| trimethylbenzenes | 21.07 |
| n-propyl toluenes | 0.11 |
| diethylbenzenes | 0.74 |
| ethylxylenes | 8.42 |
| tetramethyl benzenes | 3.05 |
| $C_{11}$ and heavier | 1.74 |

In summary when 100 parts of the 320°–410° F. fraction from the catalytically cracked stock are treated by hydrocracking followed by transalkylation the amount of material boiling below 330° F. is increased from approximately 35 parts to nearly 80 parts with little loss in liquid volume. Without hydrocracking to lower the concentration of hydrogen deficient species below 0.3 weight percent prior to transalkylation, the transalkylation catalyst would deactivate rapidly and the yield of product boiling below 330° F. would be correspondingly reduced.

EXAMPLE V

In this example, the same charge as used in Example I is hydrocracked over a catalyst containing 88% kaolin matrix containing 11.25 wt. % of rare earth exchanged zeolite Y bearing 0.75 wt. % palladium- having a silica-to-alumina mole ratio of 5. Hydrocracking conditions include: 700° F., 750 psig, LHSV 1, hydrogen to hydrocarbon mole ratio of 6:1, and hydrogen to $H_2S$ mole ratio of 250:1.

The hydrocrackate is then transalkylated at 300 psig, 600° F., 2 LHSV and a hydrogen rate of 7000 SCFB of liquid feed over the catalyst (acid leached clinoptilolite having a silica-to-alumina mole ratio of 40:1 and bearing 0.48 wt % palladium) prepared by the process of Example III of U.S. Pat. No. 3,565,788.

Although this invention has been illustrated by reference to specific embodiments, it will be apparent to those skilled in the art that various changes and modifications may be made which clearly fall within the scope of this invention.

We claim:

1. The method of treating a charge stream containing (i) at least one alkylaromatic hydrocarbon having 6–12 carbon atoms and (ii) at least one hydrogen-deficient aromatic hydrocarbon having (8+n) carbon atoms and less than (10+2n)/(8+n) atoms of hydrogen per atom of carbon wherein $n$ is an integer 0–8 which comprises hydrocracking said charge stream at aromatic ring maintaining conditions in the presence of hydrogen and at least one heterogenous solid catalyst, having a mole ratio of silica-to-alumina $SiO_2$:$Al_2O_3$ of 0–12, containing at least one metal selected from the group consisting of rhenium, Group VI B and Group VIII metals on acidic support thereby converting said hydrogen-deficient aromatic hydrocarbon having less than (10+2n)/(8+n) atoms of hydrogen per atom of carbon to more desirable aromatic hydrocarbons containing more hydrogen than said hydrogen-deficient hydrocarbons;

withdrawing from said hydrocracking operation a hydrocrackate stream containing (i) at least one alkylaromatic hydrocarbon having 6–12 carbon atoms and (ii) less than about 0.3 w % (based upon the total said product stream) of said hydrogen-deficient aromatic hydrocarbon having less than (10+2n)/(8+n) atoms of hydrogen per atom of carbon wherein $n$ is an integer 0–8;

contacting said hydrocrackate stream, at aromatic-ring-maintaining alkyl-transfer conditions, with a heterogeneous solid alkyl transfer catalyst, having mole ratio of silica-to-alumina atoms above about 12:1, and containing 0–10% of at least one Group VIII metal selected from the group consisting of nickel, cobalt, iron, platinum, palladium, rhodium, iridium, ruthenium, and osmium;

maintaining the content, in said hydrocrackate admitted to said contacting operation, of less than about 0.3 w % of said hydrogen-deficient aromatic compound thereby extending the effective life of said catalyst during said alkyl-transfer; and withdrawing product aromatic hydrocarbon from said alkyl transfer operation.

2. The method of claim 1 wherein said charge stream contains 0.3 w %–10 w % of hydrogen deficient aromatic arocarbons.

3. The method of claim 1 wherein hydrocracking is effected in the presence of at least one heterogeneous solid catalyst containing Group VIII metal on acidic support.

4. The method of claim 1 wherein hydrocracking is effected in the presence of at least one heterogeneous solid sulfided catalyst including an acidic support and having a mole ratio of silica-to-alumina of 3–8.

5. The method of claim 1 wherein hydrocracking is effected in the presence of 1 w %–10 w % fluorided alumina.

6. The method of claim 1 wherein hydrocracking is effected at 400° F.–900° F.

7. The method of claim 1 hydrocracking is effected at 50–2000 psig.

8. The method of claim 1 wherein the concentration of hydrogen-deficient components in said hydrocrackate is 0–0.2 w %.

9. The method of claim 1 wherein hydrocrackate is passed directly to said alkyl transfer operation.

10. The method of claim 1 wherein hydrocrackate is passed directly to said alkyl transfer operation without intervening processing.

11. The method of claim 1 wherein said alkyltransfer operation is transalkylation.

12. The method of claim 1 wherein said alkyltransfer operation is transalkylation effected in liquid phase at 500° F.–800° F.

13. The method of claim 1 wherein said alkyltransfer operation is transalkylation effected in the presence of 0–10 w % of Group VIII metal on a base selected from the group consisting of (i) halided (0–10 w %) alumina and (ii) alkali metal deficient zeolite.

14. The method of claim 1 wherein said alkyltransfer operation is disproportionation.

15. The method of claim 1 wherein said hydrocracking operation and said alkyl transfer operation are effected at substantially the same temperature.

16. The method of claim 1 wherein said hydrocracking operation is effected in the presence of catalyst having a silica-to-alumina mole ratio of zero.

17. The method of treating a charge stream containing (i) at least one alkylaromatic hydrocarbon having 6–12 carbon atoms and (ii) at least about 0.3 w %–10 w % of hydrogen-deficient aromatic hydrocarbons having $(8+n)$ carbon atoms and less than $(10+2n)/(8+n)$ atoms of hydrogen per atom of carbon wherein $n$ is an integer 0–8 which comprises hydrocracking said charge stream at aromatic-ring-maintaining conditions including temperature of 400° F.–900° F. and pressure of 50–2000 psig in the presence of hydrogen and sulfur and a heterogeneous solid catalyst, having a mole ratio of silica-to-alumina $SiO_2:Al_2O_3$ of 3–8 containing at least one metal selected from the group consisting of rhenium, Group VI B and Group VIII metal on acid support, thereby converting said hydrogen-deficient aromatic hydrocarbons having less than $(10+2n)/(8+n)$ atoms of hydrogen per atom of carbon to more desirable aromatic hydrocarbons containing more hydrogen than said hydrogen-deficient hydrocarbon;

withdrawing from said hydrocracking operation a hydrocrackate stream containing (i) alkylaromatic hydrocarbons having 6–12 carbon atoms, and (ii) less than about 0.3 w % (based upon the total said product stream) of said hydrogen deficient aromatic hydrocarbons having less than $(10+2n)/(8+n)$ atoms of hydrogen per atom of carbon wherein $n$ is an integer 0–8;

transalkylating said hydrocrackate stream at aromatic-ring-maintaining conditions including temperature of 500° F.–800° F. and pressure of 100–2000 psig in the presence of hydrogen and sulfur and a heterogenous solid catalyst having a silica-to-alumina mole ratio $SiO_2:Al_2O_3$ of 30–60;

maintaining the content, in said hydrocrackate admitted to transalkylation, of less than about 0.3 w % of said hydrogen-deficient aromatic hydrocarbon compounds thereby extending the effective life of said catalyst during said transalkylation; and withdrawing product aromatic hydrocarbon from said transalkylation operation.

* * * * *